US011512329B2

(12) United States Patent
Lin et al.

(10) Patent No.: US 11,512,329 B2
(45) Date of Patent: Nov. 29, 2022

(54) COMPOSITIONS AND METHODS FOR PRODUCTION OF ORGANIC ACIDS

(71) Applicant: THE REGENTS OF THE UNIVERSITY OF MICHIGAN, Ann Arbor, MI (US)

(72) Inventors: Xiaoxia Nina Lin, Ann Arbor, MI (US); Ian Graves, Ann Arbor, MI (US); Jeremy Minty, Ann Arbor, MI (US); Scott A. Scholz, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 30 days.

(21) Appl. No.: 16/283,110

(22) Filed: Feb. 22, 2019

(65) Prior Publication Data
US 2019/0264243 A1  Aug. 29, 2019

Related U.S. Application Data

(60) Provisional application No. 62/634,460, filed on Feb. 23, 2018.

(51) Int. Cl.
*C12P 7/56* (2006.01)
*C12P 7/46* (2006.01)
*C12N 1/14* (2006.01)
*C12P 19/02* (2006.01)

(52) U.S. Cl.
CPC .............. *C12P 7/56* (2013.01); *C12N 1/14* (2013.01); *C12P 7/46* (2013.01); *C12P 19/02* (2013.01); *C12P 2203/00* (2013.01)

(58) Field of Classification Search
CPC .... C12P 7/56; C12P 7/46; C12P 19/02; C12P 2203/00; C12N 1/14
USPC ........................................................ 435/139
See application file for complete search history.

(56) References Cited

U.S. PATENT DOCUMENTS

| 4,963,486 A | 10/1990 | Hang et al. | |
|---|---|---|---|
| 2011/0183389 A1 | 7/2011 | Walsum et al. | |
| 2013/0330791 A1* | 12/2013 | Milos ..................... | A23K 10/38 435/136 |
| 2015/0197777 A1 | 7/2015 | Adhikari et al. | |
| 2017/0321233 A1 | 11/2017 | Medoff | |

FOREIGN PATENT DOCUMENTS

| WO | WO2004063382 A2 | 7/2004 |
|---|---|---|
| WO | WO2012071392 A2 | 5/2012 |
| WO | WO2014013509 A2 | 1/2014 |
| WO | WO2015011285 A2 | 1/2015 |

OTHER PUBLICATIONS

Mondala, Direct fungal fermentation of lignocellulosic biomass into itaconic, fumaric, and malic acids: current and future prospects, J Ind Microbiol Biotechnol, vol. 42, (2015), p. 487-506.*
Huang et al., Optimization of ellagic acid production from ellagitannins by co-culture and correlation between its yield and activities of relevant enzymes, Bioresource Technology, vol. 99, (2008), pp. 769-775.*
Brijwani et al., Production of a cellulolytic enzyme system in mixed-culture solid-state fermentation of soybean hulls supplemented with wheat bran, Process Biochemistry, vol. 45, (2010), pp. 120-128.*
Hackbart et al., Reduction of aflatoxins by Rhizopus oryzae and Trichoderma reesei, Mycotoxin Res (2014) 30:141-149.*
Hutchinson et al., Nutritive Value of Wheat Bran, J. Sci., Fd Agric., (1970), vol. 21, March.*
Griffith et al., Copper deficiency in potato dextrose agar causes reduced pigmentation in cultures of various fungi, FEMS Microbiol Lett, vol. 276, (2007), pp. 165-171.*
Brethauer, et al., Consolidated bioprocessing of lignocellulose by a microbial consortium. Energy Environ. Sci. 2014; 7:1446-1453.
Carroll, et al., Cellulosic biofuels. Annu Rev Plant Biol. 2009;60:165-82.
Den Haan, et al., Progress and challenges in the engineering of non-cellulolytic microorganisms for consolidated bioprocessing. Curr Opin Biotechnol. Jun. 2015;33:32-8.
Deshpande, MV., Ethanol production from cellulose by coupled saccharification/fermentation using *Saccharomyces cerevisiae* and cellulase complex from Sclerotium rolfsii UV-8 mutant. Appl Biochem Biotechnol. Sep. 1992;36(3):227-34.
Ding, et al., Production of fumaric acid by Rhizopus oryzae: role of carbon-nitrogen ratio. Appl Biochem Biotechnol. Aug. 2011;164(8):1461-7.
Dorsam et al., Sustainable Carbon Sources for Microbial Organic Acid Production With Filamentous Fungi. Biotechnol Biofuels. Oct. 23, 2017;10:242. 12 pages.
Dunn, et al., Land-use change and greenhouse gas emissions from corn and cellulosic ethanol. Biotechnol Biofuels. Apr. 10, 2013;6(1):51.
Juhasz, et al., Characterization of cellulases and hemicellulases produced by Trichoderma reesei on various carbon sources. Process Biochem. 2005; 40:3519-3525.
Kautola, et al., Fumaric acid production from xylose by immobilized Rhizopus arrhizus cells. Appl. Microbiol. Biotechnol. 1989; 31:448-452.
Kawaguchi, et al., Bioprocessing of bio-based chemicals produced from lignocellulosic feedstocks. Curr Opin Biotechnol. Dec. 2016;42:30-39.
Kim, et al., Cellulosic ethanol production using a yeast consortium displaying a minicellulosome and β-glucosidase. Microb Cell Fact. Feb. 5, 2013;12:14.
Kumar, et al., Physical and chemical characterizations of corn stoverand poplar solids resulting from leading pretreatment technologies. Bioresour Technol. Sep. 2009;100(17):3948-62.
Lambertz, et al., Challenges and advances in the heterologous expression of cellulolytic enzymes: a review. Biotechnol Biofuels. Oct. 18, 2014;7(1):135.
Minty, et al., Design and characterization of synthetic fungal-bacterial consortia for direct production of isobutanol from cellulosic biomass. Proc Natl Acad Sci U S A. Sep. 3, 2013;110(36):14592-7.

(Continued)

*Primary Examiner* — Jennifer M. H. Tichy
(74) *Attorney, Agent, or Firm* — Casimir Jones, S.C.; Tanya A. Arenson

(57) ABSTRACT

Provided herein are compositions and methods for production of organic acids. In particular, provided herein are consolidated bioprocessing compositions and methods for single reactor production of organic acids.

2 Claims, 2 Drawing Sheets

(56) References Cited

OTHER PUBLICATIONS

Moreno, et al., A review of biological delignification and detoxification methods for lignocellulosic bioethanol production. Crit Rev Biotechnol. 2015;35(3):342-54.
Olson, et al., Recent progress in consolidated bioprocessing. Curr Opin Biotechnol. Jun. 2012;23(3):396-405.
Parisutham, et al., Feasibilities of consolidated bioprocessing microbes: from pretreatment to biofuel production. Bioresour Technol. Jun. 2014;161:431-40.
Peterson, et al., Trichoderma reesei RUT-C30—thirty years of strain improvement. Microbiology. Jan. 2012;158(Pt 1):58-68.
Roa Engel, CA, et al., Fumaric acid production by fermentation. Appl Microbiol Biotechnol. Mar. 2008;78(3):379-89.
Scholtz et al., Production of Cellulosic Organic Acids via Synthetic Fungal Consortia. Biotechnol Bioeng. Apr. 2018;115(4):1096-1100.
Valkonen, et al., Intracellular pH responses in the industrially important fungus Trichoderma reesei. Fungal Genet Biol. Sep. 2014;70:86-93.

* cited by examiner

COMPOSITIONS AND METHODS FOR PRODUCTION OF ORGANIC ACIDS

This application claims the benefit of U.S. provisional application Ser. No. 62/634,460, filed Feb. 23, 2018, which is incorporated herein by reference in its entirety.

FIELD OF DISCLOSURE

Provided herein are compositions and methods for production of organic acids. In particular, provided herein are consolidated bioprocessing compositions and methods for single reactor production of organic acids.

BACKGROUND OF THE DISCLOSURE

Lignocellulosic biomass is an attractive substrate for bioconversion into industrial chemicals because it is the most abundant terrestrial renewable bio-feedstock on earth. As a non-edible plant substrate, lignocellulose can be produced as agricultural and forest residues, which do not require massive land use changes. There are also strong social motivations for using lignocellulosic biomass as a replacement for edible substrates currently used for industrial bioconversions, such as corn and simple sugars (Dunn et al., *Biotechnol. Biofuels* 6:51 2013). However, due to the recalcitrant nature of lignocellulose to enzymatic hydrolysis, it has not been widely used as an industrial feedstock (Carroll and Somerville, *Annu. Rev. Plant Biol.* 60:165-82 2009).

What is needed are efficient and cost-effective strategies for conversion of biomass into commercially useful products such as organic acids.

SUMMARY OF THE DISCLOSURE

Provided herein are compositions and methods for production of organic acids. In particular, provided herein are consolidated bioprocessing compositions and methods for single reactor production of organic acids.

Consolidated bioprocessing is a potential breakthrough technology for reducing costs of biochemical production from lignocellulosic biomass. Production of cellulase enzymes, saccharification of lignocellulose and conversion of the resulting sugars into a chemical of interest occur simultaneously within a single bioreactor. Described herein are compositions and methods that overcome deficiencies in existing bioprocessing methods to yield an efficient and low cost method of producing organic acids from biomass.

Accordingly, in some embodiments, provided herein is method of producing an organic acid, comprising: a) contacting, in a single bioreactor, a biomass source, a first fungus that generates monomeric sugars from said biomass, and a second fungus that generates an organic acid from said monomeric sugars. In some embodiments, the biomass is cellulose or alkaline pre-treated corn stover. In some embodiments, the cellulose is lignocellulosic biomass. In some embodiments, the first fungus is *Trichoderma* sp. (e.g., *Trichoderma reesei*). In some embodiments, the second fungus is *Rhizopus* sp. (e.g., *Rhizopus delemar* or *Rhizopus oryzae*). In some embodiments, the organic acid is fumaric acid or lactic acid. In some embodiments, the bioreactor does not comprise yeast extract or cellulase enzymes. In some embodiments, the bioreactor further comprises a co-culture medium. In some embodiments, the co-culture medium comprises nitrogen.

Further embodiments provide a kit or system, comprising one or more or all of: a single bioreactor comprising a biomass source, a first fungus that generates monomeric sugars from said biomass, and a second fungus that generates an organic acid from said monomeric sugars.

Certain embodiments provide a kit, composition, or system comprising a biomass source, a first fungus comprising a *Trichoderma* sp. (e.g., *Trichoderma reesei*), and a second fungus comprising a *Rhizopus* sp. (e.g., *Rhizopus delemar* or *Rhizopus oryzae*).

Additional embodiments are described herein.

DEFINITIONS

Figure 1:
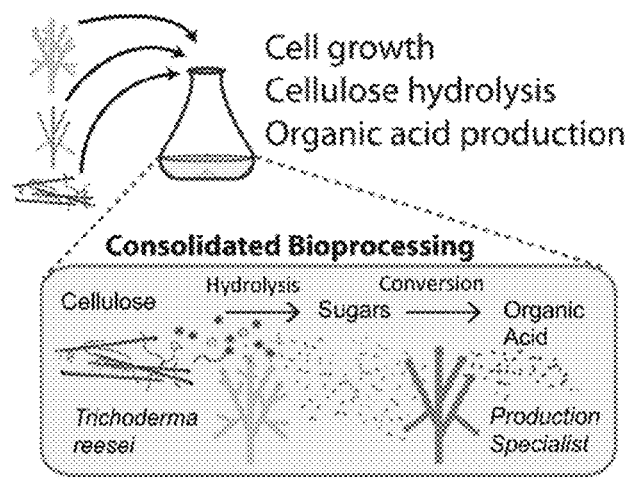
FIG. 1 shows an overview of an exemplary consolidated bioprocessing (CBP) system for organic acid production.

To facilitate an understanding of the present invention, a number of terms and phrases are defined below:

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "microbe" refers to a microorganism and is intended to encompass both an individual organism, or a preparation comprising any number of the organisms.

As used herein, the term "microorganism" refers to any species or type of microorganism, including but not limited to, bacteria, archaea, fungi, protozoans, mycoplasma, and parasitic organisms.

As used herein, the term "fungi" is used in reference to eukaryotic organisms such as the molds and yeasts, including dimorphic fungi.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

DETAILED DESCRIPTION OF THE DISCLOSURE

Provided herein are compositions and methods for production of organic acids. In particular, provided herein are consolidated bioprocessing compositions and methods for single reactor production of organic acids.

Consolidated bioprocessing (CBP) has been widely discussed as a strategy for improving the efficiency of converting lignocellulosic biomass into industrial biochemicals (Brethauer and Studer, *Energy Environ. Sci.* 7:1446-1453 2014; Kawaguchi et al., *Curr. Opin. Biotechnol.* 42:30-39 2016; Parisutham et al., *Bioresour. Technol.* 161:431-440 2014; herein incorporated by reference in their entireties). In CBP enzyme production, enzymatic hydrolysis of lignocellulose and conversion of resulting sugars to biochemicals occur simultaneously in a single reaction vessel, resulting in significant potential cost savings (Olson et al., *Curr. Opin. Biotechnol.* 23:396-405 2012). One approach for CBP has been to genetically engineer a single microorganism to produce cellulases and convert sugars into desired biochemicals. However, the efficiency of cellulase production, secretion and activity remains a major obstacle to this approach (den Haan et al., *Curr. Opin. Biotechnol.* 33:32-38 2015; Lambertz et al., *Biotechnol. Biofuels* 7:135 2014; herein incorporated by reference in their entireties).

Additionally, the requirement for tremendous new efforts of engineering a single microorganism to produce a new chemical of interest has made this approach difficult from a practical standpoint. Recently, a number of CBP systems have been designed to combine more than one microorganism. In these approaches, two or more microorganisms are cultured together, typically dividing the tasks of hydrolysis and biochemical production between microbial specialists. These systems are more modular, allowing different chemicals to be produced without major genetic redesigns. Several groups have successfully designed synthetic consortia-based CBP strategies for producing ethanol (Brethauer and Studer, 2014, supra; Goyal et al., *Microb. Cell Fact.* 10:89 2011; Kim et al., *Microb. Cell Fact.* 12:14 2013). A synthetic consortium CBP system has also been designed for the production of isobutanol from lignocellulosic biomass by pairing the cellulolytic fungus *Trichoderma reesei* with an engineered isobutanol-producing *Escherichia coli* strain (Minty et al., *Proc. Natl. Acad. Sci. U.S.A.* 110:14592-14597 2013; herein incorporated by reference in its entirety).

The present disclosure overcomes these obstacles to provide a consolidated bioprocessing method for production of organic acids from cellulose biomass. In exemplary experiments described herein, synthetic fungal consortia composed of the cellulolytic fungus *Trichoderma reesei* and the production specialist *Rhizopus delemar* demonstrated conversion of microcrystalline cellulose (MCC) and alkaline pre-treated corn stover to fumaric acid in a fully consolidated manner without addition of cellulase enzymes or expensive supplements such as yeast extract. A titer of 6.87 g/L of fumaric acid, representing 0.17 w/w yield, were produced from 40 g/L MCC with a productivity of 31.8 mg/L/h. In addition, lactic acid was produced from MCC using a fungal consortium with *Rhizopus oryzae* as the production specialist.

The present disclosure is not limited to the production of particular metabolites. In some embodiments, systems and methods described herein find use in the production of organic acids (e.g., including but not limited to, fumaric or lactic acid).

In some embodiments, the present disclosure provides a single bio-rector method of consolidated bioprocessing that utilizes two different fungi to produce organic acids without the need for expensive co-factors such as yeast extract. In order to arrive at the described combination of fungi and culture conditions, experimentation and analysis of choice of fungi and reaction conditions were utilized.

In some embodiments, systems and methods utilize two fungi, a first species that is cellulolytic and a second species that produces organic acids. The present disclosure is not limited to particular first and second fungi. In some exemplary embodiments, the first fungus is *Trichoderma* sp. (e.g., *Trichoderma reesei*). In some embodiments, the second fungus is *Rhizopus* sp. (e.g., *Rhizopus delemar* or *Rhizopus oryzae*).

The present disclosure is not limited to particular substrates. In some embodiments, the substrate is a biomass. In some embodiments, the biomass is cellulose or alkaline pre-treated corn stover. In some embodiments, the cellulose is lignocellulosic biomass.

In some embodiments, culture conditions are optimized for consolidated fermentation. For example, in some embodiments, the concentration of nitrogen in the culture medium is optimized for production of organic acids. For example, when the biomass source does not include high levels of nitrogen, nitrogen levels are increased in the culture medium. If the biomass has high levels of nitrogen, the amount of nitrogen in the media can be decreased in order to promote production of organic acids. In some embodiments, culture medium is free of yeast extract or cellulose enzymes.

In some embodiments, culture occurs in a bioreactor or other suitable flask or culture container. The term "bioreactor," includes any suitable vessel, or section within a vessel, for maintaining a liquid volume of culture medium with microorganisms that may be used to carry out the biological processes described herein. Particular types of bioreactors can include any vessels suitable for two-phase (gas-liquid) contacting, for example counter-current flow reactors (e.g., with an upwardly-flowing vapor phase and downwardly-flowing liquid phase) or co-current flow reactors (e.g., with upwardly-flowing gas and liquid phases). In such two-phase contacting vessels, it is possible for the liquid phase to be the continuous phase, as in the case of gas bubbles flowing through a moving column of liquid. Otherwise, it is possible for the vapor phase to be the continuous phase, as in the case of a dispersed liquid (e.g., in the form of droplets) flowing through a vapor space.

Specific examples of bioreactors include Continuous Stirred Tank Reactors (CSTRs), Immobilized Cell Reactors (ICRs), Trickle Bed Reactors (TBRs), Moving Bed Biofilm Reactor (MBBRs), Bubble Columns, Gas Lift Fermenters, and Membrane Reactors such as Hollow Fiber Membrane Bioreactors (HFMBRs). Suitable bioreactors may include static mixers, or other vessels and/or devices (e.g., towers or piping arrangements), suitable for contacting the gaseous Cl-containing substrate with the liquid bacterial culture medium (e.g., with dissolution and mass transport kinetics favorable for carrying out the biological conversion). The phrases "plurality of bioreactors" or bioreactors that may be included in a "plurality of bioreactor stages" are meant to include bioreactors of more than a single type, although in some cases the plurality of bioreactors may be of one type (e.g., circulated loop reactors).

Typically cells are grown at a temperature in the range of about 25° C. to about 40° C. in an appropriate medium (e.g., those described herein). Other defined or synthetic growth media may also be used. Suitable pH ranges for the fermentation are between pH 5.0 to pH 9.0. In some embodiments. In some embodiments, fermentations are performed under aerobic conditions.

Fermentation may be performed under batch or continuous methods of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Batch fermentations are described, for example, in Thomas D. Brock in Biotechnology: A Textbook of Industrial Microbiology, Second Edition (1989) Sinauer Associates, Inc., Sunderland, Mass., or Deshpande, Mukund V., Appl. Biochem. Biotechnol., 36:227, (1992), herein incorporated by reference in their entireties.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Further embodiments provide a composition, kit or system, comprising one or more or each of a single bioreactor comprising a biomass source, a first fungus that generates monomeric sugars from said biomass, and a second fungus that generates an organic acid from said monomeric sugars. In some embodiments, kits comprise one or more of cofactors, media (e.g., co-culture media described herein), and the like.

EXPERIMENTAL

The following example is provided in order to demonstrate and further illustrate certain preferred embodiments and aspects of the present invention and are not to be construed as limiting the scope thereof.

Example 1

Materials and Methods

*Trichoderma reesei* strain RaVC was generously provided by Mari Valkonen of the VTT Technical Institute (Finland) (Valkonen et al., *Trichoderma reesei. Fungal Genet. Biol.* 70:86-93 2014). *Rhizopus delemar* (NRRL 1526) and *Rhizopus oryzae* (NRRL 395) were provided by the ARS culture collection (United States Department of Agriculture). Alkaline pre-treated corn stover was provided by the National Renewable Energy Laboratory (Golden, Colo.) with the following composition of non-soluble solids: ash 7.3%, ligin 17.8%, glucan 47.8%, xylan 21.2%, galactan 1.1%, arabinan 2.5%, acetate 0.1%. A slurry of the material was subjected to vacuum on Whatman #1. 1.6 mL deionized water per gram of slurry was applied to the biomass and immediately removed by vacuum filtration. The resulting biomass was dried for 48 hours under vacuum. *T. reesei, R. delemar* and *R. oryzae* spores were generated on potato dextrose agar (PDA) at 30° C. for 10 days. Spores were harvested and stored in 20% glycerol at −80° C. indefinitely. Production cultures were grown in *Rhizopus-Trichoderma* co-culture medium (RTco) (0.5 g/L $(NH_4)_2SO_4$, 0.125 g/L Urea, 0.6 g/L $CaCl_2$, 0.4 g/L $MgSO_4 \times 7H_2O$, 0.3 g/L $KH_2PO_4$, 44 mg/L $ZnSO_4 \times 7H_2O$, 10 mg/L $FeSO_4 \times 7H_2O$, 2 mg/L $CoCl_2 \times 6H_2O$, 1.6 mg/L $MnSO_4 \times 4H_2O$, 0.0186% Tween-80 (v/v)) unless otherwise noted. Sterile $MgSO_4$, $CaCl_2$ and $FeSO_4$ solutions were added immediately before culture seeding, yielding the appropriate final RTco medium concentrations, in order to prevent precipitation. Trichoderma Minimal Medium (TMM) (Minty et al., 2013, supra) with a modified 11.76 mM nitrogen concentration was used for lactic acid production. *T. reesei* spores from cryostock were inoculated into 10 mL potato dextrose broth (PDB) and grown for 2 days at 30° C. with shaking in a 50 mL conical tube to generate a pre-culture. Mycelia from the pre-culture were pelleted at 4600×g for 6 minutes and washed once in nitrogen-free RTco medium. 250 µL of mycelia resuspended in 10 mL of nitrogen-free RT-co medium were inoculated into 25 mL RTco medium with 20 g/L microcrystalline cellulose (MCC) and grown for 2 days in a 125 mL baffled flask to generate an adjustment culture. The adjustment culture was used to seed production cultures at 1% of total volume. *R. delemar* or *R. oryzae* were seeded from PDA spore slants stored for less than 2 months into 100 mL RTco medium with 20 g/L glucose and grown for 16 hours in a 500 mL baffled flask with shaking to generate a pre-culture. Mycelia from the pre-culture were pelleted at 4600×g for 6 minutes. Half of the mycelia from the resulting pellet was inoculated into 100 mL fresh RTco medium with 3 g/L glucose and grown for 3.5 hours in a 500 mL baffled flask with shaking to generate an adjustment culture. The adjustment culture was used to seed production cultures at 1% of total volume. Production cultures were grown using 25 mL RTco medium in 125 mL baffled flasks at 30° C. with 225 rpm shaking. Sterilization of the media was achieved through autoclaving for 15 minutes at 121° C. Glucose, fumaric acid and lactic acid concentrations were determined by HPLC (Agilent 1100 with RID-10A detector equipped with a Rezexi™ ROA-Organic Acid H+ (8%) column). All reported yield and productivity values were calculated from the time point with the highest titer for the compound of interest.

Results

In this example, synthetic fungal consortia were designed to produce fumaric and lactic acids from cellulose and lignocellulosic biomass. *T. reesei* was used as a cellulitic specialist because of its extensively documented efficient cellulase enzyme production and conversion of cellulose into monomeric sugars in minimal media (FIG. 1) (Peterson and Nevalainen, *Microbiology* 158:58-68 2012). Therefore, production specialist candidates were assessed based on efficient bioconversion of sugars into organic acids in similar minimal media. Factors such as temperature, aeration and culture conditions were considered for compatibility. Finally, production specialists previously demonstrating the highest yields and titers of organic acids were prioritized. Using these criteria, Rhizopus delemar (fumaric acid) and Rhizopus oryzae (lactic acid) were selected as production specialists for synthetic consortia CBP. In each CBP system, the hydrolysis and production processes occur simultaneously. Carbon is liberated from cellulose by cellulase enzymes produced by T. reesei and the resulting sugars are immediately converted into organic acids by the production specialist in the same bioreactor (FIG. 1). The successful design and implementation of synthetic consortia CBP for production of fumaric and lactic acid represents a significant step towards establishing a robust, versatile, and modular platform technology for consortia-based CBP conversion of lignocellulosic biomass to a wide variety of biochemicals.

Figure 2:
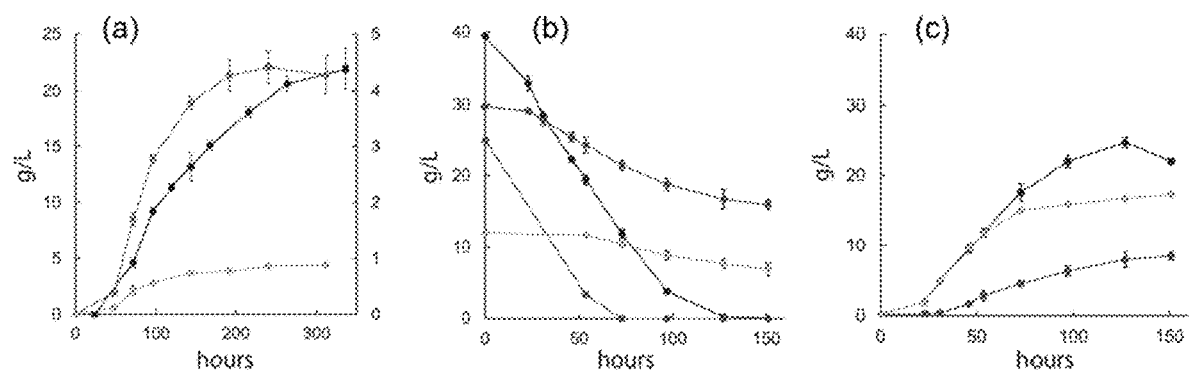
FIG. 2 shows that monocultures exhibit efficient specialist activities in medium formulated for co-culture. A) Sugar accumulation by *T. reesei* in two monoculture experiments: glucose; glucose and xylose from 20 g/L alkaline pretreated corn stover. B) *R. delemar* monoculture can utilize pure glucose, pure xylose, or a mix of glucose and xylose in RTco medium. C) *R. delemar* production of fumaric acid from sugar substrates corresponding to B).

A defined minimal medium Rhizopus-Trichoderma co-culture medium (RTco) was formulated to allow both cellulose hydrolysis and fumaric acid production without the need for supplementation with expensive components such as yeast extract. R. delemar switches from growth to fumaric acid production phase when nitrogen is no longer available in culture media (Ding et al., Appl. Biochem. Biotechnol. 164:1461-1467 2011). Therefore, RTco was formulated with a nitrogen concentration that is 12.5% of those commonly used for T. reesei growth and cellulase production (Juhász et al., Process Biochem. 40:3519-3525 2005; Minty et al., 2013, supra). Under these conditions, both fungi are expected to grow until nitrogen becomes limiting in the production medium, at which point growth and cellulase production would cease, while fumaric acid production begins. Each fungal strain was first characterized in monocultures with the RTco medium. Monocultures of T. reesei grown on 40 g/L microcrystalline cellulose (MCC) in RTco medium efficiently accumulated glucose as expected (FIG. 2A). Under the consortia CBP conditions 22 g/L of glucose is produced from MCC at a productivity of 65 mg/L/h after 336 hours fermentation time. Monocultures of T. reesei were also grown on 20 g/L alkaline pre-treated corn stover (CS) in RTco medium. The CS utilized is composed of 47.8% and 21.2% of non-soluble glucan and xylan by weight, respectively. Glucan and xylan account for 95% of the carbohydrates in the CS. It was observed that 4.4 g/L glucose accumulated from hydrolysis of the CS, representing 41% of the theoretical maximum yield from glucan, while 0.86 g/L xylose accumulated, representing 15% of the theoretical maximum yield from xylan. Total sugar productivity was 22 mg/L/h over the course of 240 hours. R. delemar monoculture efficiently consumed 40 g/L glucose in RTco medium (FIG. 2B) to produce 22 g/L fumaric acid (FIG. 2C), representing a yield of 0.55 w/w and a productivity of 153 mg/L/h. The theoretical maximum yield of fumaric acid is two moles per mole of glucose upon fixation of two moles of $CO_2$ in a reductive carboxylation pathway. By weight, 1.29 grams of fumaric acid would be produced per gram of glucose. However, this production pathway would not allow for production of ATP and requires $CO_2$ fixation (Roa Engel et al., Appl. Microbiol. Biotechnol. 78:379-89 2008). Nitrogen concentration controls the tradeoff between cell growth and fumaric acid production (Ding et al., 2011, supra). With minimal glucose substrate directed to cell growth, yields of up to 0.85 w/w from glucose have been reported. Consistent with previous observations with similar fungal strains (Kautola and Linko, Appl. Microbiol. Biotechnol. 31:448-452 1989), R. delemar was also capable of utilizing xylose as the sole or a portion of the carbon source in RTco medium to produce fumaric acid, albeit more slowly than on glucose. Additionally, R. delemar grown on medium containing mixed glucose and xylose demonstrated usage of both sugars and accumulation of fumaric acid (FIGS. 2B and C). Results described above demonstrate the compatibility of T. reesei and R. delemar to be grown together for consolidated conversion of cellulose to fumaric acid in RTco medium.

Figure 3:
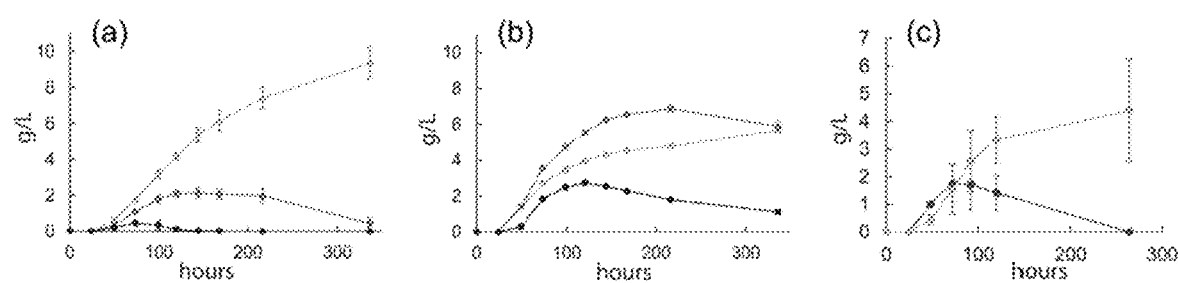
FIG. 3 shows CBP conversion of MCC to organic acids by synthetic fungal consortia. A) Glucose accumulation under low (5.88 mM), medium (11.76 mM), and high (23.5 mM) nitrogen conditions. B) Fumaric acid accumulation with nitrogen concentrations corresponding to A). C) Lactic acid production from 40 g/L MCC using a modified fungal consortium.

The tradeoff between fumaric acid production rate and yield from glucose by R. delemar can be controlled by nitrogen concentration (Ding et al., 2011, supra). R. delemar monocultures with high nitrogen concentrations lead to more R. delemar cell growth and higher subsequent production rates of fumaric acid, but achieve lower final yields. Likewise, in consortium CBP the nitrogen concentration can also control the amount of carbon that is utilized for cell growth versus carbon directed towards producing fumaric acid. Therefore, nitrogen concentration should be a key parameter for optimizing the T. reesei-R. delemar consortium CBP system. To test whether the proposed fungal consortium can produce fumaric acid from cellulose and whether nitrogen can control production dynamics as expected, consortium performance was monitored in RTco medium with three nitrogen concentrations. Nitrogen concentration variation led to different culture dynamics and production titer, yield and productivity (FIG. 3). Production medium with a low 5.88 mM nitrogen concentration allowed for relatively high amounts of glucose accumulation (FIG. 3A) and slow fumaric acid production, eventually achieving 0.148 yield by MCC weight and 16.6 mg/L/h productivity (FIG. 3B). Comparatively, an intermediate nitrogen concentration of 11.76 mM led to slow initial glucose accumulation and a decrease in glucose concentration at later time points, due to conversion into fumaric acid. Fumaric acid production under intermediate nitrogen concentration condition outperformed the other nitrogen concentrations tested in terms of yield (0.17 by weight), productivity (31.8 mg/L/h) and titer (6.87 g/L). In medium with the highest nitrogen concentration tested, 23.5 mM, almost no glucose accumulation was detected, fumaric acid accumulation was delayed, and the fumaric acid yield reached only 0.137 by weight. These results are consistent with a greater proportion of carbon being allocated for fungal growth under higher nitrogen conditions. Under optimal process control only low concentrations of glucose accumulated, indicating that the rate of sugar liberation from MCC by T. reesei closely matches the rate of sugar conversion into fumaric acid by R. delemar without actually limiting conversion due to sugar limitation.

A lactic acid-producing consortium CBP system was designed by replacing R. delemar with R. oryzae (NRRL 395). Experiments were performed using the same nitrogen concentration in TMM medium. Lactic acid titer of 4.4 g/L, representing a 0.11 w/w yield and 16.7 mg/L/h productivity, was achieved (FIG. 3C).

Figure 4:
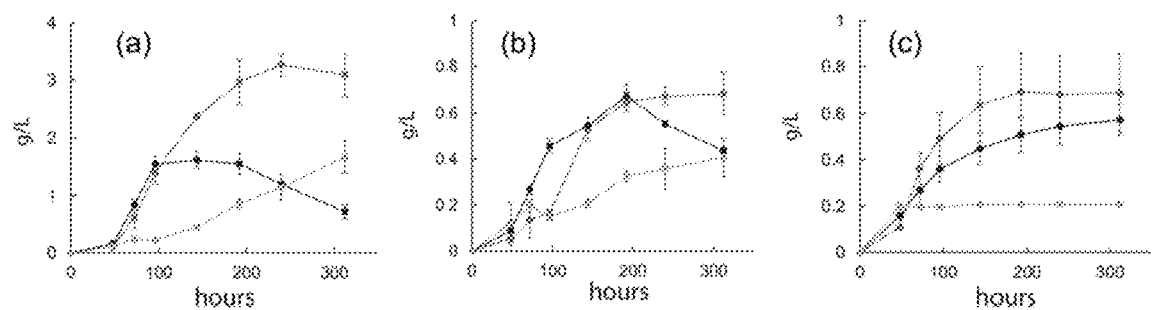
FIG. 4 shows fumaric acid production from alkaline pre-treated corn stover by fungal consortium at different nitrogen concentrations. A) Glucose accumulation under zero, low (2.9 mM), and high (5.88 mM) added nitrogen conditions. B) Xylose accumulation with nitrogen concentrations corresponding to A). C) Fumaric acid accumulation with nitrogen concentrations corresponding to A). Nitrogen added as a medium component is lower for all corn stover conditions in comparison to MCC experiments. Error bars represent the standard deviation of 4 replicates.

Next, consortium performance was investigated on alkaline pre-treated corn stover (CS). Lignocellullosic biomass is a complex substrate composed of crystalline cellulose, hemicellulose and lignin. In addition to these carbon compounds, nitrogen from proteins and other plant structures is present in all lignocellulosic biomass. Since nitrogen concentration controls the flow of carbon between fungal growth and fumaric acid production, the amount of nitrogen added to the culture medium must complement the useable nitrogen derived from the lignocellulosic biomass substrate. The fungal consortium was seeded into RTco medium containing 20 g/L of CS, which is composed of 9.6 g/L and 4.2 g/L of glucan and xylan respectively, under three different nitrogen concentration conditions. Similar to the performance on MCC, high nitrogen conditions led to fast substrate degradation and earlier cessation of fumaric acid production compared to lower nitrogen conditions (FIG. 4). The high nitrogen condition used for these experiments was 5.88 mM, much lower than in the MCC experiments, but led to similar consortium dynamics. The difference between optimal nitrogen concentrations using MCC versus CS substrates are likely due to CS-derived nitrogen. A previous study showed that similarly treated corn stover contained 0.6% elemental nitrogen (Kumar et al., *Bioresour. Technol.* 100:3948-3962 2009), which would correspond to about 9 mM nitrogen in these cultures. It should be noted, however, only an unknown fraction of this total nitrogen is metabolizable by the fungi. 0.69 g/L of fumaric acid was produced with a yield of 0.05 by weight from total initial fermentable carbohydrates. Overall consortium performance was considerably lower compared to those for MCC as the carbon substrate. As observed in numerous previous studies, this reduction in performance is likely due to inhibitory compounds from the lignocellulosic biomass (Moreno et al., *Crit. Rev. Biotechnol.* 35:342-354 2015). Although *R. delemar* is a promising consortium candidate because it efficiently converts sugars into fumaric acid and satisfies the major fungal consortia requirements, its acid production performance was low on CS. *T. reesei* was relatively much more tolerant of the corn stover substrate, producing 0.46 w/w yield of glucose from total initial glucan solids and 0.21 w/w yield of xylose from total initial xylan solids in monoculture (FIG. 2A). Similar to approaches taken for yeast, selection of Rhizopus strains for lignocellulosic biomass tolerance may enable more efficient production (Moreno et al., 2015, supra).

Synthetic consortia were designed to convert lignocellulosic biomass to fumaric or lactic acids. Together, *T. reesei* and *R. delemar* produced up to 6.87 g/L fumaric acid from 40 g/L MCC in a CBP scheme without expensive supplements such as enzymes or yeast extract. Another consortium of *T. reesei* and *R. oryzae* demonstrated production of 4.4. g/L lactic acid from MCC. Additionally, 0.69 g/L fumaric acid was produced using CS.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. A method of producing an organic acid selected from the group consisting of fumaric acid and lactic acid, comprising:
    contacting, in a single bioreactor, a biomass source selected from the group consisting of cellulose or alkaline pre-treated corn stover, a first fungus that generates monomeric sugars from said biomass, wherein said first fungus is *Trichoderma reesei* and a second fungus that generates an organic acid from said monomeric sugars, wherein said second fungus is *Rhizopus delemar* or *Rhizopus oryzae*; and a co-culture medium comprising nitrogen at a concentration of 2.9 mM when said biomass source is alkaline pre-treated corn stover and 11.76 mM when said biomass source is cellulose.

2. The method of claim 1, wherein said bioreactor does not comprise yeast extract or exogenous cellulase enzymes.

\* \* \* \* \*